United States Patent [19]
Eugster

[11] Patent Number: 6,057,359
[45] Date of Patent: May 2, 2000

[54] SPONTANEOUSLY DISPERSIBLE CONCENTRATES COMPRISING ESTERS OF BACCATIN-III COMPOUNDS HAVING ANTITUMOR AND ANTIVIRAL ACTIVITY

[75] Inventor: Carl Eugster, Riehen, Switzerland

[73] Assignee: Marigen S.A., Riehen, Switzerland

[21] Appl. No.: 08/872,984

[22] Filed: Jun. 11, 1997

Related U.S. Application Data

[63] Continuation of application No. PCT/CH96/00329, Sep. 24, 1996.

[51] Int. Cl.$^7$ ........................ A61K 31/335; C07D 305/14
[52] U.S. Cl. .......................... 514/449; 549/510; 549/511; 424/450; 424/489; 424/502
[58] Field of Search ........................... 514/449; 549/510, 549/511; 424/450, 489, 502

[56] References Cited

U.S. PATENT DOCUMENTS

| | | | |
|---|---|---|---|
| 5,478,860 | 12/1995 | Wheeler et al. | 514/449 |
| 5,580,889 | 12/1996 | Mayhew et al. | 514/449 |
| 5,739,016 | 4/1998 | Hanson et al. | 435/117 |

FOREIGN PATENT DOCUMENTS

| | | |
|---|---|---|
| 0 559 019 | 9/1993 | European Pat. Off. . |
| 0 569 281 | 11/1993 | European Pat. Off. . |
| 0 636 618 | 2/1995 | European Pat. Off. . |
| 44 00 843 | 7/1995 | Germany . |
| 2 283 973 | 5/1995 | United Kingdom . |
| 91/01139 | 2/1992 | WIPO . |
| 92/12989 | 8/1992 | WIPO . |
| 92/21670 | 12/1992 | WIPO . |
| 94/04519 | 3/1994 | WIPO . |
| 94/07878 | 4/1994 | WIPO . |
| 94/07880 | 4/1994 | WIPO . |
| 94/17050 | 8/1994 | WIPO . |
| 94/17051 | 8/1994 | WIPO . |
| 94/18186 | 8/1994 | WIPO . |
| 94/22856 | 10/1994 | WIPO . |
| 95/16441 | 6/1995 | WIPO . |
| 95/18605 | 7/1995 | WIPO . |
| 96/03394 | 2/1996 | WIPO . |
| 97/03651 | 2/1997 | WIPO . |

OTHER PUBLICATIONS

Eugster et al., "Marigenol–Concentrates Comprising Taxol and/or Taxan esters as active Substances" *Panminerva Medica* 38:234–242 (1996).

Benita et al. "Submicron Emulsions as Colloidal Drug Carriers for Intravenous Administraction:Comprehensive Physicochemical Characterization" *Journal of Pharmaceutical Sciences* 82:1069–1079 (1993).

Pauwels et al. "Sensitive and rapid assay on MT–4 cells for detection of antiviral compounds against the AIDS virus" *Journal of Virological Methods* 16:171–185 (1987).

Bergamini et al. "A tetrazolium–based colorimetric assay for quantification of HIV–1–induced cytopathogenicity in monocyte–macrophages exposed to macrophagecolony–stimulating factor" *Journal of Virological Methods,* 40, pp. 275–286, 1992.

Levy, HIV research: a need to focus on the right target *The Lancet* 345:1619–1621 (1995).

Chan et al., "Taxa–4(16)–diene–5α,9α, 10β, 13α–tetraol, a New Taxane Derivative from the Heartwood of Yew (*T. baccata* L):X–Ray Analysis of a p–Bromobenzoate Derivative" *Chemical Communications* pp. 923–925, No. 24, 1966.

Della Casa De Marcano et al. "The Structure of Baccatin–III, a Partially Esterified Octahydroxy–monoketo–taxane Derivative Lacking a Doble Bond at C–4" *Chemical Communications* pp. 216–217, 1970.

Della Casa De Marcano et al. "Structure of Some Taxane Diterpenoids, Baccatins–III, IV,—VI, and VII and 1–Dehydroxybaccatin–IV, Possessing an Oxetan Ring" *J.C.S. Chem. Comm.* pp. 365–366 (1975).

Fleming et al., "Biosynthesis of Taxoids, Mode of Attachment of the Taxol Side Chain" *J. Am. Chem. Soc.* 116:4137–4138 (1994).

Gisler et al. "Mode–selective dynamic light scattering: theory versus experimental realization" *Applied Optics* 34:3546–3553 (1995).

Appendino et al., 14β–Hydroxy–10–deacetylbaccatin III, a New taxane from Himalayan Yew (*Taxus wallichiana* Zucc.) *J. Chem. Soc. Perkin Trans. 1* pp. 2925–2929 (1992).

Appendino et al., "New Oxetane–type Taxanes from *Taxus wallichiana* Zucc." *J. Chem Soc. Perkin Trans 1* pp. 1563–1566 (1993).

*Primary Examiner*—Ba K. Trinh
*Attorney, Agent, or Firm*—Foley & Lardner

[57] ABSTRACT

Spontaneously dispersible concentrates comprising new esters of Baccatin-III, 10-Deacetylbaccatin-III and 14-OH-10-Deacetylbaccatin-III, procedures for their production. The preparation of aqueous ultramicroemulsions, their incorporation into pharmaceutical compositions having antitumor, antiviral and virucidal activity, are efficacious in the treatment of eczemae and psoriasis and stimulate the increased absorption of exogenous activators, regulators or modulators, are described.

15 Claims, No Drawings

SPONTANEOUSLY DISPERSIBLE CONCENTRATES COMPRISING ESTERS OF BACCATIN-III COMPOUNDS HAVING ANTITUMOR AND ANTIVIRAL ACTIVITY

This application is a Continuation of co-pending PCT application number PCT/CH96/00329, filed Sep. 24, 1996.

The present invention concerns spontaneously dispersible concentrates comprising esters with Baccatin-III compounds, procedures for their production, the preparation of ultramicroemulsions and the use of these concentrates for the manufacture of medicaments which have antitumor, antiviral and virucidal activity, are efficacious in the treatment of eczemae and psoriasis and stimulate the increased absorption of exogenous activators, metabolic modulators and regulators.

The inventive esters of Baccatin-III, 10-Deacetylbaccatin-III and 14-OH-10-Deacetylbaccatin-III possess an excellent antitumor, antiviral and/or virucidal efficacy. They can also be used for the treatment of eczemae, psoriasis and metabolic disorders. The therapeutic properties of these esters manifest themselves particularly strongly, if and when they have been incorporated into spontaneously dispersible concentrates and thereafter diluted with distilled water or 5%-glucose solution or physiologic sodium salt solution (Ringer solution). In this way, they form thermodynamically stable ultramicroemulsions generating micelles with a hydrodynamic radius of 2.2 to 3.0 nm. Such ultramicroemulsions possess unprecedented kinetic properties. Thanks to the very small particle size of the micelles, they can penetrate the plasma-membrane of tumor cells and of virus-bearing cells and spread inside the cell; they evidence an excellent efficacy-to-safety relationship.

DESCRIPTION OF THE INVENTION

The inventive esters of Baccatin-III, of 10-Deacetylbaccatin-III and of 14-OH-10-Deacetylbaccatin-III correspond to the general formulae (I) to (III):

wherein at least one of $R^3$ and/or $R^4$ of the formulae (I) and (II) are replaced with a $C_{6-32}$ alkylcarbonyl, a $C_{6-32}$ alkenylcarbonyl or a $C_{6-32}$ alkapolyenecarbonyl group, and at least two of $R^1$, $R^3$ and/or $R^4$ in of the formula (III) are replaced with a $C_{6-32}$ alkylcarbonyl, a $C_{6-32}$ alkenylcarbonyl or a $C_{6-32}$ alkapolyenecarbonyl group.

Preferred are compounds in accordance with formula (I) wherein $R^1$ and $R^3$ stand for a $C_{12-22}$ alkylcarboxyl, a $C_{11-22}$ alkenylcarboxyl or a $C_{11-22}$ alkapolyenecarboxyl group.

Examples of compounds according to Formula (I) are, i.a.

7,13-Diundecenoylbaccatin-III 7,13-Dilauroylbaccatin-III 7,13-Dipalmitoylbaccatin-III 7,13-Distearoylbaccatin-III 7,13-Baccatin-III-di-oleic acid ester 7,13-Baccatin-III-di-linoleic acid ester 7,13-Baccatin-III-di-linolenic acid ester 7,13-Baccatin-III-di-arachidate 7,13-Baccatin-III-di-behenate 7-Lauroylbaccatin-III 7-Palmitoylbaccatin-III all trans-Retinoyl-7-Baccatin-III Examples of compounds according to Formulae (II) and (III) are, i.a.

10-Deacetyl-7,10-dilauroylbaccatin-III

10-Deacetyl-14β-hydroxybaccatin-7,10,14-trilaurate

10-Deacetyl-14β-hydroxybaccatin-7,10-dilaurate

10-Deacetyl-14β-hydroxybaccatin-10,14-dilaurate

The fatty-tail principle and the formation of ultramicroemulsions with TAXAN esters In recent years, several diterpenes having the unusual taxan-constitution were isolated from species of the genera Taxus, Cephalotaxus and Austrotaxus; see, e.g., S. Blechert and D. Guénard in "The Alkaloids" (Ed. A. Brossi), Vol. 39, S. 195–238, Academic Press, New York, 1990, and also M. Suffness and G. A. Cordell, ibid., Vol. 25, 1985.

Taxan-derivatives have gained great attention because of their partly excellent cancerostatic properties. The subject of the present patent document are results obtained from extensive chemical, physicochemical and biological work with the Taxan-derivatives Baccatin-III, 10-Deacetylbaccatin-III and 14-OH-10-Deacetylbaccatin-III:

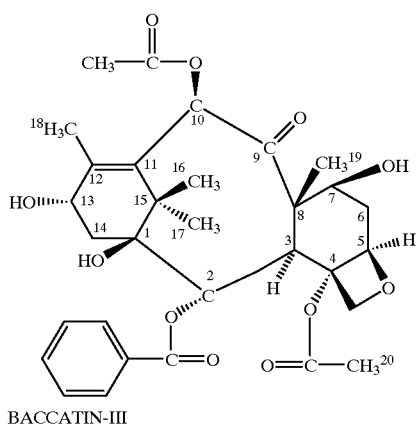

BACCATIN-III (IV)

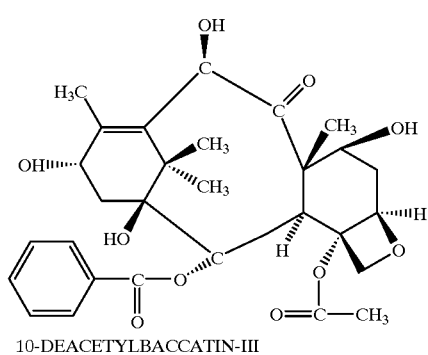

10-DEACETYLBACCATIN-III (V)

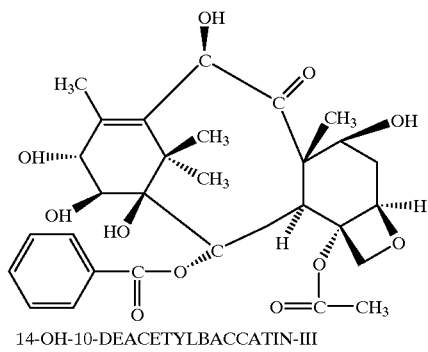

14-OH-10-DEACETYLBACCATIN-III (VI)

Baccatin-III was at first isolated from the heartwood of yew trees (*Taxus baccata*, L.), characterized and structurally identified: W. R. Chan, T. G. Halsall, G. M. Hornby, A. W. Oxford, W. Sabel, K. Bjōmer, G. Ferguson, J. Monteath Robertson, J.Chem.Soc., Chem. Comm. 1966, 923; D. P. Della Casa de Marcano, T. G. Halsall, G. M. Hornby, ibid. 1970, 216 and 1975, 365. Baccatin-III is the specific, biogenetic precursor in the plant of TAXOL [P. E. Fleming, A. R. Knaggs, X.-G. He, U. Mocek, H. G. Floss, J.Amer. Chem.Soc. 1994, 116, 4137].

In therapeutic applications, Taxol (Paclitaxel) is considered as a potent cytostatic compound [compare: Antitumor Compounds of Natural Origin: Chemistry and Biochemistry, Vol. II; Ed. Adorjan Aszalos, NCI, CRC Press, Boca Raton, 1980, pp. 170, 175] and as antitumor agent; its activity is deemed decisively stronger than that of Baccatin-III. Whether this is due to the esterification of the hydroxyl group at C(13) by substitution of cinnamic acid or to other factors, is still unclear to this day. Because of its relatively strong polarity, its high melting point and its very low solubility in water, Baccatin-III presents considerable difficulties when it is formulated into a pharmaceutical preparation for intravenous application (which is also the case for Taxol pure substance). See in this respect Blechert and Guénard, l.c., p. 232. However, Baccatin-III, and more recently also 10-Deacetylbaccatin-III, were used as starting materials for numerous partial syntheses. Also see: Kyriacos Costa Nicolaou et al.: "Chemie und Biologie von Taxol", Angew.Chem. 1994, 106, 38–69, and further Lutz Heide: "Pharmazeutische Biologie im Blickpunkt", Pharmazie in unserer Zeit/23. Jahrg. 1994/Nr. 2 (pp. 100–104). For the isolation of 14-β-Hydroxy-10-deacetylbaccatin III (ex *Taxus wallichiana*, Zucc.) compare EP 0 559 019 A1 (Indena S.p.A., Milano), Sep. 8, 1993, and E. Bombardelli and B. Gabetta, J.Chem. S., Perkin Trans. I (1992), (21), 2925–29; (1993), (14), 1563–6.

In the Swiss patent document CH 282/95 of Dec. 4, 1995/Mar. 26, 1997 it was set forth that the formulation of Taxol and of Taxol-analogues into inventive, spontaneously dispersible concentrates and the preparation of aqueous ultramicroemulsions therefrom convey to these agents significantly improved bioavailability and bioreactivity, and hence lower their relative toxicity. It was now found, that the application of the above mentioned fatty-tail principle, i.e. the esterification of Baccatin-III, of 10-Deacetylbaccatin-III and of 14-HO-10-Deacetyl-baccatin-III with longchain fatty acids, can likewise enhance their kinetics and consequently improve their pharmacological action pattern in an important way. Keeping in mind that these starting compounds can be gained from the leaves of Himalayan and other yew trees [*Taxus brevifolia*, Nutt., and *Taxus baccata*, L.] and keeping further in mind that the total synthesis of these compounds is quite cumbersome and very costly, the opportunity of making use of a biologically more readily renewable resource presents a clear advantage; felling of yew trees for the sole purpose of obtaining TAXOL-active substance can be avoided.

Baccatin-III [in accordance with formula (IV)] comprises three, structurally very distinctly reactive hydroxyl groups. In esterification reactions, as indicated in the literature, the hydroxyl group at C(7) is most readily affected; for steric reasons, the secondary, allylic group at C(13) reacts unexpectedly slowly. Due to its tertiary nature and simultaneous neopentyl position, the OH-group at C(1) is almost inattackable. If the aim is to esterify both hydroxyl groups at C(7) and C(13), then one must choose conditions, which, however, tend to simultaneously attack also the oxetan function C(4)–C(5)–C(20). In order to avoid this, we decided to use acid chlorides, which, although more reactive than anhydrides, can through the adjunction of appropriate buffer-bases be prevented from damaging the oxetan function, when in addition the generated chloride-ions are captured by means of silvercyanide. In this manner, also the reaction temperature necessary for complete reaction can be gradually raised, so that in the consequence of a suitable procedure for purification, a yield of up to 70% of pure product is achievable.

The produced esters are practically colourless and in the UV-light only weakly fluorescent. It is possible to follow the esterification reaction quite conveniently by means of TLC with coated silica gel sheets by spraying them with a cersulfate/phosphormolybdenic acid/sulfuric acid reagent, followed by heating over the mirror-burner; the ester which is sought after appears as a spot of deep sepia colour.

The produced esters can readily be incorporated into spontaneously dispersible concentrates, which after addition of distilled water, 5%-glucose-solution or physiological sodium salt solution generate stable oil-in-water-microemulsions, possessing globular micelles in the lowest nm-range.

1.0 Procedures for the Production of Compounds According to Formulae (I) to (III)

1.1 Production of 7-Baccatin III-all trans-retinoate

To 720 mg of all-trans retinoic acid in 25 ml of ether or t.butylmethylether (TBME) 360 mg of N,N'-dicyclohexylcarbodiimide (DCC) are added under cover of argon gas at 0° C. After stirring for 1 h at 0° C., 450 mg of Baccatin-III in 10 ml of ether are added dropwise. The solution is then brought to RT and stirred for another 2 h. Before distilling off the solvent, the mixture is filtered. The residue is taken up with cyclohexane/ethylacetate (95:5) as eluent and purified chromatographically on an aluminumoxide column. The 7-Baccatin-III-all trans-retinoate is obtained: $R_f$-value 0.91; UV $\lambda_{max}$ 354.0 nm.

1.2 Production of 7,13-Baccatin-III-diundecenoate

To a solution of 550 mg of Baccatin-III, 20 mg of 4-dimethylaminopyridine (DMAP) and 20 mg of N,N-dimethylformamide (DMF) in 25 ml of dichlormethane one adds dropwise at RT 600 mg (excess) of 10-undecenoyl chloride in 40 ml of dichlormethane. After stirring for 2 h the solvent is distilled off and the residue then purified chromatographically on a silica gel column using cyclohexane/ethyl acetate (95:5) as eluent. One gets the 7,13-Baccatin-III-diundecenoate; $R_f$-Value 0.85

Ester binding at 1710 cm$^{-1}$ $\nu$(C=O) Ester 1.3 Production of 7-lauroylbaccatin-III Into a well dried threeneck flask with inlet for protective gas, cooler, magnetic stirrer and septum one gives under cover of a $N_2$-atmosphere 250 mg of Baccatin-III, dissolved in 0.5 ml abs. pyridine and 5 ml 1,2-dichlorethane, and then mixed with 10 mg of 4-dimethylaminopyridine and 150 mg of very finely pulverized, dry AgCN. This mixture is cooled on the ice-bath to 0° C., and under steady stirring a solution of 2.5 equivalents (0.255 ml) of lauroyl-chloride in 5 ml of 1,2-dichlorethane is added dropwise by means of a syringe. When this operation is finished, one lets the temperature rise to RT. Subsequently the batch is warmed on the oil-bath during 18 h to ca. 45° C.

For final preparation, the suspension is mixed with Celite®, then dissolved with ether and filtered. The filtrate, which is almost colourless, gets washed repeatedly in a funnel, using some diluted sulfuric acid, then water and brine, followed by drying over $Na_2SO_4$. Using customary procedures for purification: column silica gel Merck 0.015–0.04 mm, column 2.3×20 cm; eluent ethylacetate/toluene/acetone 11:9:1, one obtains 500 mg of a pale yellow, oily honey. The intended end-product, the baccatin-monolaurate, appears relatively quickly in a narrow zone. After crystallisation from diisopropyl ether at −14° C., one obtains small, colourless bundles of needles, mp. 87–88.5° C.; yield 65–70%.

Analytical Data

HPLC almost uniform peak with $t_R$ 3.6 and $\lambda_{max}$ 242 nm on column Spherisorb S-5 CN, 4.6×250 mm, flow 0.8 ml/min. Eluent 1% B in A (A=hexane with 0.1% ethyldiisopropylamine; B=$CH_2Cl_2$ with 5% methanol).

UV ($CH_2Cl_2$): $\lambda_{max}$ 235 nm ($\epsilon$ 11'100), 277 (1'500), 285 (1'300).

$[\alpha]_D$ −60.9° ($CHCl_3$, c=0.041%; for comparison Baccatin-III=−85.5°)

IR ($CHCl_3$; cm$^{-1}$, selection of bands): 3620 and 3570s (OH): 3020, 2925, 2855m-s (methylene and methyl groups), 1733ss, broad [carbonyl groups]

Cl-MS ($NH_3$): m/z 786.4 (100%, [M+$NH_3$]$^+$)

$^1$H-NMR (CDCl$_3$, 600 MHz, δ in ppm, auxiliary methods for interpretation: $^1$H, $^1$H-DFQ-CO-SY, $^{13}$C, $^1$H-HMBC, $^{13}$C, $^1$H-HSQC, DEPT techniques). H-2: 5.62 (d, J=6.9); H-3: 3.99 (d, J=6.9); H-5: 4.96 (d, J=9.0); H-6: 1.55 and 2.6 (each m); H-7: 5.6 (dd); H-10: 6.28 (s); H-13: 4.84 (t, J=7.8); H-14: 2.3 and 2.6 (each m); $CH_3$ (16): 1.13* (s); $CH_3$ (17): 1.07* (s); $CH_3$ (18): 2.10 (s); $CH_3$ (19): 1.79 (s) $CH_2$-20: 4.43 (AB-system); $CH_3CO$-4: 2.28 (s).

$^{13}$C-NMR (selection of signals): C-4: 80.6; C-5: 84.0; C-7: 71.3; C-10: 75.8; C-11: 131.5; C-12: 144.8; C-13: 67.7; arylCO: 166.9; lauroylCO-7: 173.0; $CH_3CO$-4: 170.5; $CH_3CO$-10: 168.8; CO-9: 202.4.

In a similar way also other fatty acid esters can be produced of BACCATIN-III [in accordance with formula (IV)], of 10-DEACETYLBACCATIN-III [according to formula (V)], and of 14-OH-10-DEACETYL-BACCATIN-III [corresponding to formula VI).

1.4 Preparation of 7-Palmitoylbaccatin-III

The reaction of Baccatin-III with palmitoylchloride was done as above under 1.3; the reaction time, however, was doubled. The purification was conducted as above indicated. After recrystallisation from diisopropylether/pentane one obtains silky needles having a mp. of 77–80/90–92° C.

UV ($CH_2Cl_2$): $\lambda_{max}$ 237 nm ($\epsilon$ 19'800)

Circular dichroism ($CH_2Cl_2$, RT): 230.8 (Δε 27.0), 258.6 (0), 300.2 (−12.4).

IR ($CH_2Cl_2$: 3628w and 3570w (OH); 3049m, 2926s, 2852m (methyl- and methylene groups), 1736ss, and 1725ss [carbonyls]

$^1$H-NMR (CDCl$_3$, ARX 300): H-2: 5.63 (d J=6.7); H-3: 4.00 (d J=6.9); H-5: 4.97 (dd); H-6: 1.57 and 2.6 (each m); H-7: 5.61 (dd, partly hidden); H-10: 6.29s; H-13: 4.89 (t J=7.8); H-14: 2.2 and 2.3 (each m); $CH_3$ (16): 1.14* (s); $CH_3$ (17): 1.12* (s); $CH_3$ (18): 2.11 (d, J=1,0); $CH_3$ (19): 1.80 (s); $CH_2$-20: 4.23 (AB-system); $CH_3CO$-4: 2.28 (s).

$^{13}$C-NMR C-5: 84.1; C-7: 71.3; C-11: 131.6; C-12: 144.7; C-13: 67.9; C-14: 38.6; arylCO: 167.0; lauroylCO-7: 173.1; $CH_3CO$-4: 170.6; $CH_3CO$-10: 168.8; CO-9: 202.4.

1.5 Preparation of 10-Deacetyl-7,10-dilauroylbaccatin-III 500 mg of 10-Deacetylbaccatin-III were reacted with lauroylchloride, as above in example 1.3. The resulting raw product was purified by means of column chromatography. After crystallisation from diisopropylether at −14° C., we obtained 660 mg of the pure product, in the form of a fine, white powder, mp. 106.5–108° C.

UV ($CH_2Cl_2$): $\lambda_{max}$ 243.5 nm ($\epsilon$ 15'400)

IR ($CH_2Cl_2$: 3677w and 3608w (OH); 3006m, 2925s, 2352m (methyl and methylene groups), 1713s, broad [carbonyls]

Cl-MS ($NH_3$): m/z 926.5 (47%, [M+$NH_3$]$^+$); 909.5 (15% [M$^+$]; 804.5 (30%, [M+$NH_3$]$^+$-$H_2O$; 709.3 (100% [M$^+$-lauric acid], etc. $^1$H-NMR (CDCl$_3$, 300 MHz) : H-2: 5.62 (d, J=7.11); H-3: 3.89 (d, J=7.1); H-5: 4.99 (d with fine splitting, J=7,6); H-6: 1.7 and 2.5 (each m); H-7: 4.48 (dd, J=10,9/6, 9); H-10: 6.32 (s); H-13: 4.89 (t, J=7.5); H-14: 2.3 and ?, hidden (each m); $CH_3$ (16,17): 1.11 (s); $CH_3$ (18): 2.05 (d, J=1.0); $CH_3$ (19): 1.67 (s) $CH_2$-20: 4.23 (AB-system).

$^{13}$C-NMR (CDCl$_3$): C-1: 79.1; C-4: 80.8; C-7: 72.3; C-10: 76.4; C-11: 131.9; C-12: 146.3; C-13: 67.9; C-14: 38.6; arylCO: 167.0; $CH_3CO$-4: 170.7; lauryCO-7: 174.1; lauryCO-10: 179.0.

1.6 Esterification of 10-Deacetyl-14,β-hydroxybaccatin-III with lauroylchloride 738 mg of formula (VI) were reacted with 1,3 ml of lauroylchloride, as indicated above. Column chromatography with silica gel produced 3 main fractions, with $R_f$ 0.90; 0.53; 0.30.

(Eluent on silica gel sheets Merck: ethylacetate/toluene/acetone 11:9:1). The non-polar compound turned out as 10-Deacetyl-14β-hydroxybaccatin-III-7,10,14-trilaurate, the polar compound was 10-Deacetyl-14β-hydroxybaccatin-III-7,10-dilaurate; and the middle polar compound resulted from the close comparison of the spectra as 10-Deacetyl-14β-hydroxybaccatin-III-10,14-dilaurate.

Properties of 14-OH-10-DAB-trilaurate:

Yield: 0.1 g, colourless crystals from methanol/trace of diisopropylether at −12° C.; mp. 87–92° C.

UV ($CH_2Cl_2$): $\lambda_{max}$ 234 nm ($\epsilon$ 18'100)

Circular dichroism ($CH_2Cl_2$, RT): 229.4 ($\Delta\epsilon$ 19.2), 257.6 (0), 299.6 (−7.9)

IR 3575w OH); 2043w-m, 2853s (methylene and methyl groups), 1733ss, broad [carbonyls]

Cl-MS (with $NH_3$: m/z 1124.5 (60%, $[M+NH_3]^+$); 1107.5 (23%, $[M^+]$ 1089.5 ($M^+$-18]); 924.5 (100%, $[M+NH_3]$+-lauric acid]); 907.4 (66% $[M^+]$-lauric acid).

$^1$H-NMR ($CDCl_3$, 600 MHz): H-2: 5.75 (d, J=7.3); H-3: 3.95 (d, J=7.1); H-5: 4.90 (dd); H-6: 1.6 and 2.5 (both m); H-7: 5.56 (dd); H-10: 6.29 (s); H-13: 4.62 (s broad), 2.1 and 2.3 (both m); $CH_3$ (16): 0.98*; $CH_3$ (17): 1.12*; $CH_3$ (18): 2.08; $CH_3$ (19): 1.75 (s); $CH_2$-20: 4,18 (AB-system); $CH_3CO$-4: 2.31 (s).

$^{13}$C-NMR ($CDCl_3$): C-4: 80.5; C-5: 83.9; C-7: 71.1; C-10: 75.2; C-11: 133.1; C-12: 141.1; C-13: 76.7; C-14: 75.2; arylCO: 165.7; $CH_3CO$-4: 170.8; CO-9: 201.8; lauroylCO-7: 172.; lauroylCO-10: 171.; lauroylCO-14: 173.9.

Properties of Deacetyl-14-β-hydroxybaccatin-III-7,10-dilaurate:

Yield: 1.02 g, colourless, very thick oil, which slowly hardens to a solid mass.

UV ($CH_2Cl_2$): $\lambda_{max}$ 233 nm ($\epsilon$ 13'200)

IR 3600w and 3186w, broad (OH); 3043m, 2922ss (methylene and methyl groups), 1733ss and 1710s [carbonyls]

$^1$H-NMR ($CDCl_3$, 600 MHz) : H-2: 5.81 (d, J=7,2); H-3: 3.95 (d, J=7,1); H-5: 4.96 (d broadened, J=8,3); H-6: 1.63 and 2.41 (both m); H-7: 5.58 (dd); H-10: 6.32 (s); H-13: 4.79 (d with fine splitting, J=6,3); H-14: 4.04 (d, J=6.4); $CH_3$ (16): 1.18* (s); $CH_3$ (17): 1.07* (s); $CH_3$ (18): 2.10 (d, J=1.1); $CH_3$ (19): 181 (s); $CH_2$-20: 4.25 (AB-system); $CH_3CO$-4: 2.31 (s).

$^{13}$C-NMR ($CDCl_3$): C-1: 76.6; C-2: 74.0; C-3: 46.4; C-4: 80.7; C-5: 83.9; C-7: 71.2; C-10: 75.3; C-11: 132.7; C-12: 146.9; C-13: 75.9; C-14: 74.0; C-15: 42.8; $CH_3$ (16): 21.9*; $CH_3$ (17): 26.1*; $CH_3$ (18): 14.9; $CH_3$ (19): 10.8; $CH_2$-20: 76.2; arylCO: 166.2; $CH_3CO$-4: 170.5; lauroylCO-7: 173.2; lauroylCO-10: 173.2.

Properties of Baccatin-III-10,14-Dilaurate:

Yield 60 mg; colourless crystals from diisopropylether at −14° C.; mp. 93–103° C.

UV ($CH_2Cl_2$): $\lambda_{max}$ 234 nm ($\epsilon$ 15'800).

2.0 MARIGENOL®-Concentrates and Aqueous Ultramicroemulsions

The esters of selected Baccatin-III compounds, produced in accordance with the formulae (I) to (III), surprisingly possess excellent antitumor and antiviral/virucidal potential and can be used for the treatment of eczemae and psoriasis, if they are properly solubilized. After incorporation into inventive, spontaneously dispersible MARIGENOL®-concentrates and dilution with distilled water, 5%-glucose solution of physiological sodium salt solution (Ringer solution), it is possible to generate thermodynamically stable oil-in-water-ultramicroemulsions.

Such ultramicroemulsions possess more or less globular micelles having a hydrodynamic radius of 2.2 to 3.0 nm. [Measurement conducted with QLS=quasi-elastic, dynamic light scattering; tests performed at the Federal Institute for Technology, Zurich, Institute for Polymers (Prof. Dr. Pier Luigi LUISI and Prof. Dr. Peter SCHURTENBERGER)]. See: "Mode-selective dynamic light scattering; theory versus experimental realization", Thomas Gisler, et al., Applied Optics/Vol. 34, No. 18/Jun. 20, 1995, pp. 3546–3553.

The tensides and cotensides are capable at the phase-boundary of the microemulsion of hindering SELF-DIFFUSION. This means that no mixing takes place between the outer aqueous phase of the microemulsion and its inner, oily phase, which contains the ester compounds according to formulae (III) [and possibly other pharmaceutical active principles], solubilized in the coemulgator. In the inner, oily phase, the molecules of the selected active ingredients are thus present in monomeric or in oligomeric form.

The core of the micelles is coated by a tenside layer or bilayer; these particles are thus enabled to penetrate through the "defective" plasma membrane of the tumor cell or the virus-infected host cell, and also through the envelope of viruses. The fractal dimension of such membranes is considerably higher than that of healthy cells. The penetration process takes place on account of thermal molecular movements exclusively.

The volume and the speed of substance transport across the cell membranes are dependent upon the differential in concentration existing between the extracellular outside and the inside of the individual tumour or virusbearing cell. The diffusion flow continues along the concentration gradient until it is consumed and an equal concentration of active substance [or of a therapeutic system's preparation] is reached in both compartments, the extracellular zone and the internal zone. Such diffusion processes occur independently of any energy input from outside into the interacting compartments. They can show slow-release-effects. In biological systems they are not related to metabolic energy. The velocity of the diffusion process across the cell membrane is governed by:

1. the concentration difference in the two compartments outside and inside the cell
2. the radius of the particles of the diffusing active substance or system's preparation
3. the viscosity of the diffusing aqueous solution (emulsion)
4. the temperature.

The proper solubilization of those active substances, which are insoluble in water, by means of surfactants (coemulgator plus tensides) is a conditio sine qua non for achieving self-diffusion and hence active transport of the biologically effective substances across the membranes of living cells. As can be seen from the table, one globular micelle having a hydrodynamic radius of one centimeter possesses a volume of 4.189 $cm^3$ and a phase surface of 12.564 $cm^2$. In contradistinction: a number of $10^{18}$ micelles having each a hydrodynamic radius of $10^{-6}$ cm (=10 nm) only, together possess the same volume of 4.189 $cm^3$ and yet cover up a total phase surface of 1'256.4 $m^2$.

MICELLES: PROPORTION BETWEEN VOLUME AND SURFACE AREA

| NUMBER of the MICELLES | Hydrodynamic RADIUS of the micelles | VOLUME of the micelles | TOTAL SURFACE AREA of the micelles |
|---|---|---|---|
| 1 | 1 cm | 4.189 cm$^3$ | 12.546 cm$^2$ |
| $10^3$ | 0.1 cm = 1 mm | " | 125.64 cm$^2$ |
| $10^6$ | 0.01 cm | " | 1'256.4 cm$^2$ |
| $10^9$ | 0.001 cm | " | 12'564 cm$^2$ |
| $10^{12}$ | 0.0001 cm = 1 µm = 1'000 nm | " | 125'640 cm$^2$ |
| $10^{15}$ | 0.00001 cm = 100 nm | " | 1'256'400 cm$^2$ |
| $10^{18}$ | 10 nm | " | 1'256.4 m$^2$ |
| $10^{21}$ | 1 nm | " | 12'564 m$^2$ |

Spheric volume = $4/3\, \pi\, r^3$
Spheric surface = $4\, \pi\, r^2$

Conclusion

Due to the enormous total surface area, which is taken up in the inventive ultramicroemulsions by the micelles having a hydrodynamic radius of 2.2 to 3.0 nm, in addition to the increased diffusion capability, also the rheological distribution (the "spreading") is significantly enhanced. Hence, the bioavailability, as well as the bioreactivity of the antitumor/antiviral agents comprised in the micelles (maintained in their core in monomeric or oligmeric solution), is also decisively improved. This will allow a considerable reduction of the critical dosage required. This, in turn, causes a lowering or even complete elimination of unwanted, disturbing side-effects.

The "packing density" achieved with the spontaneously dispersible, stable MARIGENOL®-Concentrates obeys the exponential relationship illustrated above: the smaller the particle size of the micelles, the greater the packing density obtainable. Of decisive importance is the correct formation of the inner phase, its balanced proportion with respect to the entire concentrate and the choice of the suitable tensides.

3.0 Composition of the Inventive Concentrates

The spontaneously dispersible concentrates in accordance with the invention comprise:

- 0.5 to 5% by weight of an ester in accordance with the formulae (I) to (III), or of a combination of such esters, and
- 0 to 5% by weight of one or several pharmaceutical active substances as listed hereafter,
- 5 to 25% by weight of a hydrotropic agent or coemulgator, which is pharmaceutically acceptable,
- 50 to 90% by weight of a pharmaceutically acceptable surfactant or surfactant mixture, and optionally
- up to 10% by weight of a vitamin or provitamin,
- up to 10% by weight of a penetration enhancer, radical scavenger and/or stabilizer.

By the term pharmaceutical active substances are designated in the present case all active compounds which are currently being used therapeutically in human medicine. The list comprehends notably:

Beta-Blockers
Pindolol [1-(4-Indolyloxy)-3-isopropylamino-2-propanol]
Propanolol [1-Isopropylamino-3-(1-naphthyloxy)-2-propanol]
Oxprenolol [1-(o-Allyloxyphenoxy)-3-isopropylamino-2-propanol]
Metoprolol [Di-{(+−)-1-(isopropylamino)-3-[p-{2-methoxyethyl)phenoxy-2-propanol]-L (+)tartrate}]
Labetalol [5-[1-Hydroxy-2{(1-methyl-3-phenylpropyl-aminoethyl}salicylamide]

Diuretica
Acetazolamide [5-Acetamido-1,3,4-thiadiazol-2-sulfonamide]
Hydrochlorothiazide [6-Chloro-3,4-dihydro-2H-1,2,4-benzothiadiazin-7-sulfonamide-1,1-dioxide]
Chlortalidone [1-Oxo-3-(3-sulfamyl-4-chlorophenyl)-3-hydroxyisoindoline]
Metolazon [7-Chlor-1,2,3,4-tetrahydro-2-methyl-4-oxo-3-o-tolyl-6-quinazolinesulfonamide]

Mild Sedatives
Diazepam [7-Chloro-1,3-dihydro-1-methyl-5-phenyl-2H-1,4-benzodiazepin-2-one]
Medazepam [7-Chloro-2,3-dihydro-1-methyl-5-phenyl-1H-1,4-benzodiazepine]

Strong Tranquillizers
Sulpiride [N-(1-Ethyl-2-pyrrolidinyl-methyl)-2-methoxy-5-sulfamoylbenzamide]

Muscle Relaxants
Baclofen [β-(Aminomethyl)-p-chlorhydrocinnamic acid]

Antibiotics
Sulfamethoxazol [5-Methyl-3-sulfanilamido-isoxazole]
Trimethoprim [2,4-Diamino-5-(3,4,5-trimethoxybenzyl)-pyrimidine]
Chloramphenicol [D(−)-threo-2-dichlor-acetamido-1-(4-nitrophenyl)-1,3-propandiol]
Cefaclor [3-Chloro-7-D(2-phenyl-glycinamido)-cephalosporan acid monohydrate]
Cefradin [7-{D-2-Amino-2-(1,4-cyclohexadien-1-yl)-acetamido)-3-methyl-cephalosporan acid]
Bacampicillin [1-Ethoxycarbonyloxy-ethyl-6-(D-α-aminophenylacetate-amido)-penicillinate]
Minocycline [7-Diethylamino-6-desoxy-6-desmethyltetracycline]
Sulfadoxine [N'-(5,6-Dimethoxy-4-pyrimidinyl)-sulfanilamide]
Sulfamethixazole [3-Methyl-3-sulfanilamidoisoxazole]
Sulfisoxazole [3,4-Dimethyl-5-sulfanilamidoisoxazole]
Sulfadimethoxin [2,4-Dimethoxy-6-sulfanilamido-1,3,diazine]

Dermatologica
Chlorquinaldol [5,7-Dichlor-8-hydroxy-chinaldine]
Crotamiton [N-Crotonyl-N-ethyl-o-toluidene]
Diamthazol [6(−)2-Dimethylamino-ethoxy-(β-diaethylamino-)-benzothiazol-dihydrochloride]
Flumethasone-pivalate [6α,9-Difluoro-11β,17,21-trihydroxy-16α-methyl-pregna-1,4-diene-3,20,dione-21-pivalate]
Tretinoin [Vitamin-A-acid]

Corticosteroids
Cortisone [17α-21,Dihydroxy-pregn-4-en-3,11,20-triene-21-acetate]
Prednisone [11β-17,21-Trihydroxy-pregna-1,4-diene-3,20-dione]
Dexamethasone [9-Fluoro-11β,17,21-dihydroxy-16α-methyl-pregna-1,4-diene-3,20-dione]
Desoxycorton-acetate [21-Hydroxy-pregn-4-en-3,20-dione-acetate]

Coronary Agents

Pentaerythrityltetranitrate (PETN)
Nitroglycerin (Glyceryl trinitrate)
Pindolol [1-(4-Indolyloxy-3-isopropylamino-2-propanol]
Endocrine Regulation
Melatonin [N-{2-(5-Methoxy-1H-indol-3yl)ethyl}acetamide]; N-acetyl-5-methoxytryptamine
Cytostatica
Melphalan [p-Di-(2-chloroethyl)-amino-L-phenylalanine]
Procarbazine [p-(N'-Methyl-hydrazinomethyl)-N-isopropyl-benzamide]
Dactinomycin [Actinomycin D]
Polyestradiolphosphate
Cyclophosphamide [N,N-bis-(β-Chlorethyl)-amino-1-oxa-3-aza-2-phosphocyclohexane-2-oxide]
Antiinflammatory Agents
Mefenamine acid [3-Xylyl-2-aminobenzoic acid]
Dexamethasone [9-Fluoro-11β,17,21-trihydroxy-16α-methyl-pregna-1,4-diene-3,20-dione]
Hydrocortisone [17α-Hydroycorticosterone]
Coronary Dilators
Nifedipine [1,4-Dihydro-2,6-dimethyl-4-(o-nitrophenyl)-pyridine-3,5-dicarboxylic acid-dimethyl ester]
Isosorbid-dinitrate [1,4;3,6-Dianhydrosorbitol-2,5-dinitrate]
Nitroglycerine (Glyceryl trinitrate)
Dipyramidol [2,6-Bis-(diethanolamino)-4,8-dipiperidino (5,4-dipyrimidine)]
Peripheric Vasodilators
Cinepazide [4-(-3,4,5-Trimethoxy-cinnamoyl)-1-piperazineacyl-pyrrolidine]
Cyclandelate [3,3,5-Trimethyl-cyclohexylmandelate]
Cinnarizine [1-trans-Cinnamyl-4-diphenylmethyl-piperazine]
Pentoxyfylline [3,7-Dimethyl-1-(5-oxohexyl)-xanthine]
Antirythmica
Procainamide [4-Aminobenzoic acid-β-diethylaminoethylamide]
Disopyramide [4-Diisopropylamino-2-phenyl-2-(2-pyridyl)-butyramide]
Antigout Agents
Allopurinol [1H-Pyrazolo-(3,4-d)-pyrimidin-4-ol]
Antiepileptica
Phenytoin {Diphenylhydantoin}; [5,5-Diphenyl-2,4-imidazolidine-dione]
Carbamazepine [5-Carbamoyl-5H-dibenz(b,f)azepine]
Antihistaminica
Chlorphenamine [{3-(p-Chlorphenyl)-3-(2-pyridyl)-propyldimethylamine]
Clemastine {Hydrogenfumarate}; [1-Methyl-2-{2-(α-methyl-p-chloro-diphenylmethoxy)ethyl}pyrrolidine]
Mequitazine [10-(3-Quinuclidinylmethyl)phenothiazine]
Alimemazine [10-(3-Dimethylamino-2-methyl-propyl)-phenothiazine]
Agents Against Indisposition and Dizziness
Domperidone [5-Chloro-1-{1-(3-[2-oxo-1-benzimidazol-1-yl]-propyl)-4-piperidyl}2-benzimidazolinone]
Betahistine [2-{2-Methylaminoethyl}pyridine]
Metoclopramide [4-Amino-5-chlor-N-(2-diethylamino äthyl)-2-methoxybenzamide]
Blood Pressure Reducing Agents
Reserpine [3,4,5-Trimethoxybenzoyl-methylreserpate]
Rescinnamine [3,4,5-Trimethoxy-methylreserpate]
Methyldopa {L-α-Methyldopa}; [L-3-(3,4-Dihydroxyphenyl)-2-methylalanine]
Clomidinhydrochloride [2,6-Dichlor-N-2-imidazoidinyliden-benzamine hydrochloride]
Sympathomimetica
Isoproterenol [N-Isopropyl-nor-adrenaline]
Etilefrine [DL-1-{α-Ethylaminomethyl}-m-hydroxy-benzylalcohol]
Expectorantia
Carbocysteine [(S-Carboxymethyl)cysteine]
Bromhexine [N-Cyclohexyl-N-methyl-(2-amino-3,5-dibromo-benzyl)amine HCL]
L-Ethylcysteine
L-Methylcysteine
Oral Antidiabetica
Glibenclamide [N-4-2-(5-Chlor-2-methoxy-benzamido)-ethylphenylsulfonyl-N'-cyclohexyl-urea]
Tolbutamide [N-(4-Tolylsulfonyl)-N'-n-butyl-urea]
Cardiovascular Agents
Ubidecarenone
Adenosine [6-Amino-9-β-D-ribo-furanosyl-9H-purine]
Immunosuppressivum
Cyclosporin A
Antitumor Agents
Taxol (Paclitaxel)
Baccatin-III
10-Deacetylbaccatin-III
14-OH-10-Deacetylbaccatin-III
Cyclosporin D-oxide
Antiviral, Virucidal Agents (AIDS)
4-Isoleucine-Cyclosporin
Cyclosporin G
3β-Stigmast-5-en-3-laurate (β-Sitosteryl-laurate)
3β-Stigmast-5-en-3-palmitate (β-Sitosteryl-palmitate)
3β-Stigmast-5-en-3-stearate (β-Sitosteryl-stearate)
3β-Stigmast-5-en-3-arachidate (β-Sitosteryl-arachidate)
3β-Stigmast-5-en-3-behenate (β-Sitosteryl-behenate)
3β-Stigmast-5-en-3-10-undecenoate (β-Sitosteryl-10-undecenoate)
3β-Stigmast-5-en-3-oleate (β-Sitosteryl-oleate)
3β-Stigmast-5-en-3-all trans-retinoate (β-Sitosteryl-all-trans-retinoate).
(3β, 22E)-Ergosta-5,7,22-triene-3-ol-10-undecenoate [Ergosteryl-10-undecenoate, Provitamin $D_2$-undecenoate]
(3β, 22E)-Ergosta-5,7,22-triene-3-ol-laurate[Ergosteryl-laurate, Provitamin $D_2$-laurate]
(3β, 22E)-Ergosta-5,7,22-triene-3-ol-all-trans-retinoate [Ergosteryl-retinoate, Provitamin $D_2$-retinoate]
(3β, 22E)-Ergosta-5,7,22-triene-3-yl-valeric acid ester [Ergosteryl-n-valerate, Provitamin $D_2$-n-valerate]
(3β, 22E)-Ergosta-5,7,22-trien-3-yl-10-undecylenic acid ester[Ergosteryl-10-undecenoate, Provitamin $D_2$-undecenoate]
(3β, 22E)-Ergosta-5,7,22-trien-3-yl-lauric acid ester [Ergosteryl-laurate, Provitamin $D_2$-laurate]
(3β, 22E)-Ergosta-5,7,22-trien-3-yl-all-trans-retinoic acid ester[Ergosteryl-retinoate, Provitamin $D_2$-retinoate]

9,10-Secoergosta-5,7,10,(19),22-tetra-en-3-yl-valeric acid ester[Ergocalciferyl-n-valerate, Vitamin $D_2$-n-valerate]

9,10-Secoergosta-5,7,10,(19),22-tetra-en-3-yl-10-undecylenic acid ester[Ergocalciferyl-10-undecenoate, Vitamin $D_2$-undecenoate]

9,10-Secoergosta-5,7,10,(19),22-tetra-en-3-yl-lauric acid ester[Ergocalciferyl-laurate, Vitamin $D_2$-laurate]

9,10-Secoergosta-5,7,10,(19),22-tetra-en-3-yl-a.t.-retinoic acid ester[Ergocalciferyl-retinoate, Vitamin $D_2$-retinoata]

9,10-Secocholesta-5,7,10,(19),-triene-3-yl-valeric acid ester[Cholecalciferyl-n-valerate, Vitamin $D_3$-n-valerate]

9,10-Secocholesta-5,7,10,(19),-triene-3-yl-10-undecylenic acid ester[Cholecalciferyl-undecenoate, Vitamin $D_3$-undecenoate]

9,10-Secocholesta-5,7,10,(19),-triene-3-yl-lauric acid ester[Cholecalciferyl-laurate, Vitamin $D_3$-laurate]

9,10-Secocholesta-5,7,10,(19),-triene-3-yl-a.t.-retinoic acid ester[Cholecalciferyl-retinoate, Vitamin $D_3$-retinoate]

Morin-Tri-Undecenoate

Morin-Tri-Laurate

Quercetin-penta-10-undecenoate

Quercetin-pentalaurate

The surfactants or surfactant mixtures to be employed according to the invention can be anionic, cationic, ampho-teric or non-ionic. Ideally, they are non-ionic and have an HLB-value (i.e. a hydrophilic-lipophilic balance) of between 2 and 18; preferably, for mixtures, it is between 2 to 6 on the one hand and 10 to 15 on the other hand. HLB values describe the hydrophilic and lipophilic properties of an emulsifier. In this context see "Hydrophile-Lipophile Balance: History and recent Developments" by Paul Becher in Journal of Dispersion Science and Technology, 5 (1), 81–96 (1984).

Composition Example for inventive, spontaneously dispersible concentrates, which comprise active principles according to formulae (I) to (III) and which, if diluted with distilled water or 5%-glucose solution or physiological sodium salt solution (Ringer solution), automatically generate thermodynamically stable ULTRAMICROEMULSIONS, having globular micelles with a hydrodynamic radius of 2.2 to 3.0 nm.

a) 0.1 to 5% by weight of one or several active principles in accordance with formulae (I) to (III),
0 to 5% by weight of one or several pharmaceutical active substances,
5 to 25% by weight of isopropyl myristate, isopropyl palmitate or of a neutral oil, such as e.g. Miglyol® 812 (Dynamit Nobel or Hüls),
up to 45% by weight of a phosphoric acid ester surfactant, as e.g. Diphasol® 3873 (CIBA-GEIGY), Tenside 508 (CIBA-GEIGY), Zerostat® AN or AT (CIBA-GEIGY), Tinovetin® JU (CIBA-GEIGY), Soprophor® FL (RHÔNE-POULENC),
5 to 90% of Invadin JFC 800% (CIBA-GEIGY), and/or of TWEEN®-20-85 (ICI Speciality chemicals), i.e. of a polyoxyethylene-(20)-sorbitan ester tenside,
0 to 10% by weight of a vitamin or provitamin,
0 to 10% by weight of a free fatty acid, excipient, diluent, or a combination thereof.

b) 0.5 to 2% by weight of one or several active principles in accordance with formulae (I) to (III), 5 to 25% by weight of one or several biotenside esters conforming to the general formula (VII)

$$R^5\text{—COO—}R^6 \qquad (VII)$$

in which $R^5$ is a $C_{2-31}$ alkyl, a $C_{3-31}$ alkenyl or a $C_{3-31}$ alkapolyene group and $R^6$ stands for Citronellyl, Farnesyl, Geranyl, Isophytyl or Phytyl,
30 to 45% by weight of Invadin® JFC 800% and/or TWEEN®-20 [Polyoxy-ethylene sorbitan monolaurate=Polysorbate 20],
up to 45% by weight of Soprophor® FL or Diphasol® 3873.

c) 1% by weight of an agent according to formulae (I) or (III),
7% by weight of ethylalcohol ($C_2H_5OH$), glycerol or 2-propanol ($C_3H_8O$) and/or Dimethylsulfoxide (DMSO) dried,
20% of Citronellyl-10-undecenoate or Citronellyl-laurate,
30% by weight of Invadin® JFC 800% and/or TWEEN®-20,
42% of Soprophor® FL.

N.B.: INVADIN® JFC 800% (CIBA-GEIGY) is a water-free tert. octylphenyl-polyoxyethylene ether tenside, having 9 to 10 oxyethylene groups.

SOPROPHOR® FL(RHÔNE-POULENC) is a tristyrylphenolpolyoxy ethylene-18-phosphoric acid ester, TEA-salt surfactant, of formula:

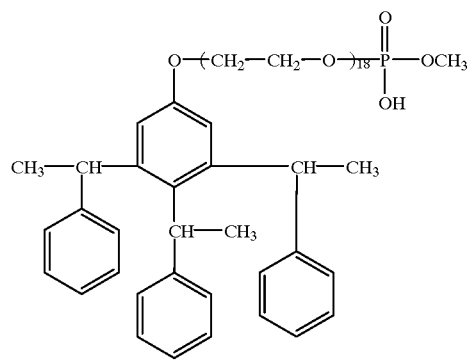

(Soprophor® FL, RHÔNE-POULENC);

TWEEN®-20-85 (ICI Speciality Chemicals) are non-ionic polyoxyethylene sorbitan ester tensides, CTFA classi-fication: Polysorbate 20-85.

The inventive oil-in-water ultramicroemulsions comprise:
0.01 to 5% by weight of the spontaneously dispersible concentrate,
85 to 99.99% by weight of distilled water, 5%-glucose solution or physiological sodium salt solution (Ringer solution or buffer),
up to 10% by weight of pharmaceutically acceptable carriers, additives, excipients and/or diluents.

Example for the pharmaceutical production of a system's preparation containing the inventive concentrates in the form of "multiple units".

a) Granulation (granules and pellets)

| | |
|---|---:|
| Metolose ® 90 SH-4000 (Shin-Etsu Chemical) | 90.0 g |
| Avicel ® PH-101 | 80.3 g |
| Inventive concentrate | 139.4 g |
| Aerosil ® 200 | 80.3 g |
| Σ | 390.0 g |

Granulation in the high speed mixer or the fluidized bed, with the addition of 110 g ethanol, sieving on a 18 to 42 mesh screen with crushing, drying for 24 h at 40° C.

b) Enteric and sustained release coating:

prepared in the fluidized bed with AQOAT® AS-HG (Shin-Etsu Chemical) and Talc.

c) Composition of finished granules or micropellets

| | |
|---|---:|
| Core Material | 44% |
| Inventive concentrate | 25% |
| Enteric coating | 31% |
| Σ | 100% |

N.B. The pellets or granules according to a) can also be filled without prior coating into capsules which are made of AQOAT® (HPMC-AS-M or HPMC-AS-N), have been sealed with acetone/ethanol 1:1 and can thus perform the functions of pH-control and slow release.

Biological Assays

The antitumour activity of spontaneously dispersible concentrates containing active substances prepared according to the processing examples 1.1 to 1.6 and according to the composition examples a) to c) is confirmed by the following test results:

1. In-Vitro Assays Using Suitable Tumour Cell Lines

A biological assay system using microtiter plates and serial dilutions has been developed. Batches of $10^4$ tumour cells per ml were set up in culture medium RPMI 1640 and inactivated with 10% of fetal calf serum (GIBCO); they are spread at a density low enough to enable them to grow during the assay, in non-confluent monolayers. Samples are added after 6 to 24 hours, with 100 μl per row, to which 100 μl of medium are added in the first well. Half of this mixture is withdrawn, transferred into the next well and again treated with 100 μl of medium, etc. This results in an n1/2 geometrical serial dilution.

In the plaque assay, the samples are incubated at 37° C. for 3 to 5 days under 3½% of $CO_2$. They are then stained and fixed using 0.1% crystal violet (Fluka, Buchs) in a solution of 70% of methanol, 1% of formaldehyde and 29% of water. The samples are evaluated under the microscope, magnification 300×. The greatest cytotoxic dilution is determined. The samples can also be evaluated quantitatively by means of scanning and absorption measurement in a spectrophotometer.

2.0 Test of Cell Toxicity

2.1 Cytotoxicity of MARIGENOL ®-CONCENTRATES tested with Py6 cells (Virus transformed 3T3 mouse-fibroblasts)

| TESTED CONCENTRATE comprising as ACTIVE SUBSTANCE | MICRO-EMULSION ME 1:100 ACTIVE SUBSTANCE (A.S.) | EX-POSURE 24 h in dilution active up to 1: | EX-POSURE 48 h in dilution active up to 1: | EX-POSURE 72 h in dilution active up to 1: |
|---|---|---:|---:|---:|
| TAXOL-A.S. | ME 1:100 | 64'000 | 256'000 | 256'000 |
| | A.S. | 6.4 Mio. | 25.6 Mio. | 25.6 Mio. |
| BACCATIN III-A.S. | ME 1:100 | 128'000 | 128'000 | 1 Mio. |
| | A.S. | 12.8 Mio. | 12.8 Mio. | 100 Mio. |
| BACCATIN III-7,13-DE-UNDE-CENOATE | ME 1:100 | 128'000 | 256'000 | 1 Mio. |
| | A.S. | 12.8 Mio. | 25.6 Mio. | 100 Mio. |
| 7,13-BACCATIN III-DI-LAURATE | ME 1:100 | 128'000 | 128'000 | 256'000 |
| | A.S. | 12.8 Mio. | 12.8 Mio. | 25.6 Mio. |
| 7,13-BACCATIN III-all trans-RETINOATE | ME 1:100 | 128'000 | 256'000 | 256'000 |
| | A.S. | 12.8 Mio. | 25.6 Mio. | 25.6 Mio. |

Dilutions:
First row given as concentrate-dilution 1:100 = aqueous microemulsion (M.E.)
Second row calculated on active substance-content N.B.: On the subject of the eternalized Py6-cells cf.: "Biochemistry", Coordinating Editor Geoffrey L. Zubay, Addison-Wesley Publishing Company, 1983, p.1079.

2.2 Cytotoxicity: Comparative assays conducted with other, highly potent natural compounds and with their esters, respectively (correspondingly formulated as 1%-MARIGENOL ®-CONCENTRATES) tested on Py6-cells (Polyoma-Virus transformed 3T3 mouse fibroblasts)

| TESTED CONCENTRATE comprising as A.S. (ACTIVE SUBSTANCE) | MICRO-EMULSION ME 1:100 ACTIVE SUBSTANCE (A.S.) | EX-POSURE 24 h in dilution active up to 1: | EX-POSURE 48 h in dilution active up to 1: | EX-POSURE 72 h in dilution active up to 1: |
|---|---|---:|---:|---:|
| TAXOL-A.S. | ME 1:100 | 64'000 | 256'000 | 256'000 |
| | A.S. | 6.4 Mio. | 25.6 Mio. | 25.6 Mio. |
| BACCATIN III-A.S. | ME 1:100 | 128'000 | 128'000 | 1 Mio. |
| | A.S. | 12.8 Mio. | 12.8 Mio. | 100 Mio. |
| BACCATIN III-DI-UNDECENOATE | ME 1:100 | 128'000 | 256'000 | 1 Mio. |
| | A.S. | 12.8 Mio. | 25.6 Mio. | 100 Mio. |
| BACCATIN III-DI-LAURATE | ME 1:100 | 128'000 | 128'000 | 256'000 |
| | A.S. | 12.8 Mio. | 12.8 Mio. | 25.6 Mio. |
| BACCATIN III-a.t.-RETINOATE | ME 1:100 | 128'000 | 256'000 | 256'000 |
| | A.S. | 12.8 Mio. | 25.6 Mio. | 25.6 Mio. |
| MORIN-PENTA-LAURATE | ME 1:100 | 128'000 | 1 Mio. | 1 Mio. |
| | A.S. | 12.8 Mio. | 100 Mio. | 100 Mio. |
| MOREN-PENTA-PALMITATE | ME 1:100 | 64'000 | 512'000 | 512'000 |
| | A.S. | 6.4 Mio. | 51.2 Mio. | 51.2 Mio. |
| CHRYSIN-DI-LAURATE | ME 1:100 | 128'000 | 512'000 | 1 Mio. |
| | A.S. | 12.8 Mio. | 51.2 Mio. | 100 Mio. |
| CHRYSIN-DI-PALMITATE | ME 1:100 | 128'000 | 512'000 | 512'000 |
| | A.S. | 12.8 Mio. | 51.2 Mio. | 51.2 Mio. |
| QUERCETIN-PENTA-UNDECENOATE | ME 1:100 | 256'000 | 1 Mio. | 2 Mio. |
| | A.S. | 25.6 Mio. | 100 Mio. | 200 Mio. |

Dilutions:
First row given as concentrate-dilution 1:100 = aqueous microemulsion (M.E.)
Second row calculated on active substance-content (A.S.)

3.0 Analytical Detection 3.1 Identification of Baccatin III-ester-active Substance
By capillary zone electrophoresis with an instrument of BECKMAN INSTRUMENTS P/ACE 2100 or of BIORAD.

Conditions: Buffer pH=7.0

50 mM sodium phosphate 100 mM boric acid 50 mM SDS filtered 0.2 µm

To 20 ml of this buffer were added 5 ml of methanol

Capillary: HP bubble cell 15 µm Ø, 37 cm, 10 sec. pressure injection

Run 15 kV–70 µA, measurement at 195 nm

Detection limit 0.5 ppm.

Depending on the viscosity of the test material, the peak appears after 27 minutes for the TAXOL-concentrate (emulgators!) and 44 minutes for pure TAXOL active substance.

And alternatively, using a fused silica capillary FS 75 µm, 50 cm same buffer conditions Run 15 kV–70 µA, measurement at 195/220 nm The peak appears after 57 minutes.

Complementary control measurements effected with UV-MALDI-Ms-spectrometry, using 2,6-Dihydroxyacetophenone as matrix. The resulting peaks correspond.

5.2 Identification of the Concentrate Micelles in the Aqueous Microemulsion and in the Cell Plasma of the Host Cells after Exposure, Respectively Same method as above under 3.1

The typical peak of the inventive ester compounds contained in the micelles appears after ca. 45–60 minutes.

5.3 Demonstration of Membrane Penetration at the Tumour Cell

With light microscopy (as well as when using electron microscopy) it can be shown that a few hours after incubation (example: Py6 virus transformed 3T3-mouse fibroblasts; thinly disseminated; medium dilution one of the inventive ester concentrates) a corona of vacuoles is forming around the nucleus of the host cells.

The analytical demonstration that these vacuoles in fact contain the inventive active substance is quite clear and unequivocal: it involves cleaning the incubated tumour or host cells, extracting the cell plasma with 1% SDS, centrifuging, mixing the supernatant with a 0.05%-solution of Uvitex® CF conc. (CIBA-GEIGY) in acetone/water (85:15) or of Uvitex® EBF (CIBA-GEIGY) or of Tinopal® GS (CIBA-GEIGY).

The ESTERS according to the invention extinguish the fluorescence in the longwave UV-segment which is normally occasioned by the markers Uvitex® CF conc. and Uvitex® EBF, and Tinopal® GS respectively. The thin-layer plate shows blue coloring.

Cf. also: Koji Otsuka et al.: Separation of lipophile compounds by micellar electrokinetic chromatography with organic modifiers, Electrophoresis, 1994, 15, 1280–83 (VCH Verlagsgesellschaft mbH, Weinheim).

4.0 Comparative assays with human tumor cell lines
VITALITY TEST/1%-MARIGENOL-CONCENTRATE
$1 \times 10^4$ cells per well
Proliferation test (Tritium: 1 µCi/well $H^+$)

| PREPARATION | $10^{-3}$ | | $10^{-4}$ | | $10^{-5}$ | |
|---|---|---|---|---|---|---|
| | cpm | % | cpm | % | cpm | % |
| LEUKEMIA K 562/Controls 50'037 cpm | | | | | | |
| TAXOL-A.S. | 679 | 1.3 | 830 | 1.6 | 3'553 | 7.1 |
| BACCATIN III-A.S. | 680 | 1.3 | 757 | 1.5 | 3'188 | 6.3 |
| BACCATIN III-DI-UNDECENOATE | 466 | 0.9 | 665 | 1.3 | 4'770 | 9.5 |
| BACCATIN III-DI-LAURATE | 585 | 1.1 | 651 | 1.3 | 3'060 | 6.1 |
| BACCATIN III-all trans-RETINOATE | 415 | 0.8 | 822 | 1.6 | 7'526 | 15.0 |
| LEUKEMIA DAUDI-LINE/Controls 23'090 cpm | | | | | | |
| TAXOL-A.S. | 552 | 2.3 | 672 | 2.9 | 16'090 | 69.6 |
| BACCATIN III-A.S. | 708 | 3.0 | 795 | 3.4 | 14'190 | 61.4 |
| BACCATIN III-DI-UNDECENOATE | 293 | 1.2 | 653 | 2.8 | 9'636 | 41.7 |
| BACCATIN III-DI-LAURATE | 346 | 1.4 | 455 | 1.9 | 8'851 | 38.3 |
| BACCATIN III-all trans-RETINOATE | 256 | 1.1 | 412 | 1.7 | 12'173 | 52.7 |

Tests performed by Dottoressa Anna Rita GUARINI, Università degli Studi di Torino, Clinica medica, Aug. 21–24, 1995.

5.0 General tolerance of the MARIGENOL ®-Preparations
EFFECT on the BLOOD
TOXICITY of MARIGENOL ®-Concentrates
on the BALB/c-mouse, %-Distribution of the Blood particles

| Preparation | L | M | N | E | B |
|---|---|---|---|---|---|
| G17 | | | | | |
| $10^{-7}$ | 70 ± 6 | 11 ± 3 | 13 ± 4 | 6 ± 4 | 0 |
| $10^{-5}$ | 77 ± 6 | 6 ± 3 | 11 ± 4 | 5 ± 4 | 1 ± 1 |
| $10^{-3}$ | 69 ± 10 | 7 ± 5 | 22 ± 8 | 2 ± 2 | 0 |
| G41 | | | | | |
| $10^{-7}$ | 77 ± 6 | 6 ± 3 | 13 ± 5 | 3 ± 3 | 0 |
| $10^{-5}$ | 78 ± 4 | 10 ± 2 | 10 ± 4 | 1 ± 1 | 1 ± 1 |
| $10^{-3}$ | 80 ± 6 | 8 ± 2 | 10 ± 6 | 12 ± 1 | 0 |
| G44 | | | | | |
| $10^{-7}$ | 74 ± 17 | 10 ± 1 | 20 ± 9 | 1 ± 1 | 0 |
| $10^{-5}$ | 74 ± 6 | 9 ± 4 | 14 ± 7 | 4 ± 3 | 0 |
| $10^{-3}$ | 76 ± 5 | 6 ± 4 | 16 ± 8 | 2 ± 1 | 0 |
| G55 | | | | | |
| $10^{-7}$ | 78 ± 4 | 10 ± 4 | 10 ± 4 | 2 ± 1 | 0 |
| $10^{-5}$ | 69 ± 10 | 11 ± 3 | 18 ± 4 | 1 ± 1 | 0 |

-continued 5.0 General tolerance of the MARIGENOL ®-Preparations
EFFECT on the BLOOD
TOXICITY of MARIGENOL ®-Concentrates
on the BALB/c-mouse, %-Distribution of the Blood particles

| Preparation | L | M | N | E | B |
|---|---|---|---|---|---|
| $10^{-3}$ | 77 ± 5 | 6 ± 4 | 14 ± 2 | 2 ± 1 | 1 ± 1 |
| CONTROLS (Physiological Buffer) | 76 ± 5 | 8 ± 2 | 15 ± 4 | 1 ± 1 | 0 |

G17 2%-concentrate containing $C_{5:0}$-CHOLESTERYL ESTER (Cholesteryl-iso-Valerate)
G41 2%-concentrate containing $C_{11:1}$-ERGOSTERYL ESTER (Ergosteryl-10-Undecenoate)
G44 2%-concentrate containing $C_{18:2}$-CHOLECALCIFERYL ESTER ($C_{18:2}D_3$; Vitamin $D_3$-Linoleate)
G55 2%-concentrate containing $C_{4:1}$-CHOLECALCIFERYL ESTER ($C_{4:1}$-$D_3$; Vitamin $D_3$-Crotonate)
Dilutions:
$10^{-7}$ = 0.1 ppm concentrate; 0.002 ppm active substance
$10^{-5}$ = 10.0 ppm concentrate; 0.200 ppm active substance
$10^{-3}$ = 1'000.0 ppm concentrate; 20.000 ppm active substance
(Dilutions calculated on the 2%-concentrates taken as base)
L = Lymphocytes
M = Monocytes (macrophages)
N = Neutrophile granulocytes
E = Eosinophile granulocytes
B = Basophile granulocytes Assays conducted by: Prof. Dott. Guido FORNI, Dott$^a$ Stefania VAI, Università di Torino, Dipartimento di Scienze Cliniche e Biologiche, Ospedale San Luigi Gonzaga, 1-10'043 ORBASSANO (TO), August/September 1993.

Test conducted with normal 8-weeks old female BALB/c nAncr (H-2d)-mice, supplied by Charles River Laboratories, Calco (Italy). During 4 weeks an injection i.v. was made twice per day each of 0.250 ml aqueous microemulsion, obtained from the indicated Marigenol®-Concentrates by dilution with distilled water, and of physiological buffer for the controls, respectively.

Staining with May Grünwald-Giemsa.

Duration of treatment: 28 days

Blood analysis: after the last injection

Number of animals: 13 groups of 5 animals each

RESULT: There appear no significant differences between the test groups and the controls. The concentrates possess no toxicity against the population of leucocytes under observation. All animals were and remained healthy during the whole assay.

6.0 Comparative Assays Using 2 Different Formulations

A TAXOL-A.S., formulated as a spontaneously dispersible MARIGENOL®-Concentrate, which generates an aqueous ultramicroemulsion B TAXOL-A.S., formulated as a customary concentrate (but without alcohol!), which produces an aqueous macroemulsion only C BACCATIN III-A.S., formulated as a spontaneously dispersible MARIGENOL®-Concentrate, which generates an aqueous ultramicroemulsion D BACCATIN III-A.S., formulated as a customary concentrate (but without alcohol!), which produces an aqueous macroemulsion only Test results:

| TESTED CONCENTRATE with a 1%-ACTIVE SUBST. CONTENT | MICRO-/MACRO-EMULSION 1:100 AKTICE SUBSTANCE A.S. | EXPOSURE 24 h, in DILUTION active up to 1: | EXPOSURE 48 h, in DILUTION active up tozu 1: |
|---|---|---|---|
| A: TAXOL-A.S. | EM 1:100 A.S. | 128'000 12.8 Mio. | 512'000 51.2 Mio. |
| B: TAXOL-A.S. | EM 1:100 A.S. | <4'000 <400'000 | <4'000 <400'000 |
| C: BACCATIN A.S. | EM 1:100 III-A.S. | 128'000 12.8 Mio. | 256'000 25.6 Mio. |
| D: BACCATIN A.S. | EM 1:100 III-A.S. | <4'000 <400'000 | <4'000 <400'000 |

Note that the inventive MARIGENOL®-concentrates surpass the customary formulation in decisive manner. During the short exposure time of 24 h, their bioreactivity is 30-fold higher, and with 48 h of exposure it reaches 125 times what was customary and achievable up-to-now.

The MARIGENOL®-concentrates were formulated with $C_{11:1}$-Citronellyl ester as the coemulgator and with a 1:1 tenside-mixture of Invadin JFC 800%/Soprophor FL.

Customary concentrates were prepared with isopropylmyristate as the coemulgator and with Cremophor® EL (BASF) as emulsifier, using no alcohol, however.

In all cases the proportions between A.S.:Coemulgator:Tensides were the same.

The analytical control of the diverse formulations, conducted at the Institute for Polymers at the Federal Institute for Technology, Zurich, gave the following data:

Micellar size of concentrates in microemulsion:

| PREPARATION | MICELLAR SIZE in nm |
|---|---|
| A: TAXOL-A.S. | 2.2–2.3 without filter |
| B: TAXOL-A.S. | 5–6 60–100 strong diversity broad distribution 10%-filter (90% cut-off) |
| C: BACCATIN III-A.S. | 2.2–3.0 no filter, but 75°-angle |
| D: BACCATIN III-A.S. | 4–12 strong diversity broad distribution 10%-filter |
| ESTER-COMPOUNDS: | |
| QUERCETIN-PENTA-UNDECENOATE | 2–3 |
| β-ESTRADIOL-DI-OLEATE | 2–3 |
| APIGENIN-TRILAURATE | 2–3 |
| GENISTEIN-TRILAURATE | 2–3 |

Measurement conducted with aqueous emulsions 1:100 (CMC-marginal value for a homogenous spreading of the surfactants), prepared from the 1%-concentrates. Method: dynamic light scattering (DLS) in 3 angular positions each (60°, 90° and 120°), and with 10 single measurements taken each time. The instrument is a specially equipped "Fiberoptic Spectrometer" of the Institute for Polymers. Description of the method and the instrument, see: "Mode-selective dynamic light scattering: theory versus experimental realization". Thomas Gisler et al., Applied Optics/Vol. 34, No. 18/Jun. 20, 1995.

7.0 Assays on Protective and Antiviral Effects Against HIV on MT-4 Susceptible Cells The tests were performed at the Institute of Infectious Diseases, University of TORINO, Italy, (Head: Prof. P. GIOANNINI) by Dr. Alberto BIGLINO, Head of the infectious Diseases Department, General Hospital of ASTI (Italy), with technical assistance by Dott$^a$. Brunella FORNO and Dott$^a$. Annamaria POLLONO. June/July 1994, March/April 1995.

7.1 Protective Effect on the Host Cells (MT4-Lymphocytes) Against HIV Infection

MT4-cells (an immortalized T-cell line highly sensitive to HIV cytopathoge-nic effect, CPE) of a 24 h-old culture were suspended at a concentration of $2 \times 10^5$/ml, divided into 1.2 ml aliquotes in polypropylene tubes, and pelleted by centrifugation. Pellets were either infected with 200 µl of a stock solution of HIV strain III B (Titre: 600 $CCID_{50}$/ml), or mock-infected with plain medium, for 90 min. at 37° C, upon which 1 ml of plain medium was added to each tube, restoring initial cell concentration and bringing HIV concentration to 100 $CCID_{50}$/ml. [$CCID_{50}$/ml=50% cell culture infective dose].

100 µl volumes of the MARIGENOL®-Concentrates to be tested, diluted to aqueous microemulsions $10^{-3}$ and then further diluted from $10^{-3}$ to $10^{31\ 5}$ in RPMI 1640 medium, or of plain medium, were added in triplicate to flat-bottom, 96-well microtitre plates. Each well received 100 µl of either HIV-infected or mock-infected MT-4 culture, in order to obtain 4 sets of cultures as follows:

simple culture (MT-4 cell viability control, $10^5$ cells/ml or $2 \times 10^4$/well)

culture+HIV (Virus CPE control, 50 $CCID_{50}$/ml or 10 $CCID_{50}$/well)

culture+active substance microemulsion culture +HIV+active substance microemulsion in the dilutions $10^{-3}$ to $10^{-5}$ (=1,000 ppm, 100 ppm and 10 ppm concentrate content; which corresponds to 10 ppm, 1 ppm and 0.1 ppm active substance-content).

Cultures were incubated at 37° C., in a humified atmosphere of 5% $CO_2$+95% air. Five days after infection, 100 µl of supernatant were removed from each well, and cell viability was assessed by reduction of a methyl-tetrazolium salt (MTT, Sigma, 25 µl/well of a 5 mg/ml solution) in a 2-h incubation test, followed by solubilization with 100 µl DMSO/well and photometric readout of the optical density at 550 nm. Residual cell viability was expressed as percent difference from HIV CPE-control cultures mean readout, considered as zero.

The best protective action upon the host cells could, so far, be achieved with a 1%-concentrate of β-Sitosteryl-Palmitate at a concentration of $10^{-4}$ (=100 ppm concentrate in aqueous ultramicroemulsion); very remarkable results were also obtained with concentrates comprising β-Sitosteryl-Caproylate, β-Sitosterypl-Laurate, β-Sitosteryl-Arachidate or β-Sitosteryl-Behenate.

7.2 Effect on HIV Infectivity. (Direct Antiviral Efficacy Against the Acquired Immunodeficiency Syndrome: "AIDS")

Aliquote amounts of two HIV isolates from patients (strains 21/4 and 4/5) resuspended in complete RPMI medium at a titre of 300 $CCID_{50}$/ml were incubated during 3 hours, +4° C. with MARIGENOL®-concentrate, in the form of an aqueous microemulsion, at concentrations ranging from $10^{-2}$ to $10^{-5}$ in complete medium, as well as with ("empty") carrier concentrate and with medium alone as controls.

After pre-incubation, residual HIV titre was assessed by the $CCID_{50}$ method (Cell-culture infecting dose 50%). Briefly, serial twofold dilutions were prepared from each of the six virus suspensions, and 200 µl of each dilution were incubated for 90 minutes with MT-4 cell pellets prepared as stated before (see 7.1). At the end of incubation, pellets were brought to initial cell concentration by adding appropriate amounts of complete RPMI medium to each tube, whose content was then distributed into 8 wells of a flat-bottom microtitre plate in 200 µl volumes, each vertical row coresponding to a dilution. After 5 days of incubation, cell viability was assessed by the MTT test as stated above, and the HIV titre was expressed as the reciprocal of that dilution which infects 4 out of 8 wells (50%) in a row. A well was considered infected when its O.D. readout at 550 nm was lower than the average readout of 8 control wells minus 2.8 times the standard error of the mean (lower 95% confidence limit).

Results a) Protective Effect on MT-4 Cells Against HIV-Infection

Significant protection of MT-4 cells from HIV-induced cytopathogenic effect (CPE) could be achieved with a 1% stock microemulsion of β-Sitosteryl-Palmitate at concentrations around $10^{-4}$ (=100 ppm of concentrate in aqueous ultramicroemulsion). Similar, though less remarkable results, were also obtained with stock ultramicroemulsions of β-Sitosterypl-Caproylate, β-Sitosterypl-Laurate, β-Sitosterypl-Arachidate and β-Sitosteryl-Behenate at concentrations ranging from $10^{-3}$ to $10^{-4}$.

b) Direct Antiviral Activity on HIV

The infectivity of 2 HIV strains (21/14 and 4/5) isolated from AIDS-patients was significantly inhibited by pretreament with 1%-concentrate comprising β-Sitosterypl-Palmitate, in a dose-dependent way, while a somewhat less potent inhibition was also obtained with a 1%-concentrate of Ergosteryl-10-Undecenoate. No inhibition at all became manifest after pretreatment with carrier-concentrate alone.

| TEST SUBSTRATE | RESIDUAL HIV TITRE ($CCID_{50}$) (Mean titre from 3 cultures) |
|---|---|
| HIV strain 21/4 (clinical isolate) + medium | 300 |
| HIV strain 4/5 (clinical isolate) + medium | 200 |
| HIV (2 strains) + CARRIER-CONCENTRATE | 200 (Mean titre of 2 strains) |
| HIV (2 strains) + ERGOSTERYL-10-UNDECENOATE Concentrate 1'000 ppm Active substance 10 ppm | 25 (Mean titre of 2 strains) |
| HIV (2 strains) + β-SITOSTERYL-PALMITATE Concentrate 1'000 ppm Active substance 10 ppm | 2 (Mean titre of 2 strains) |
| HIV (2 strains) + β-SITOSTERYL-PALMITATE Concentrate 100 ppm Active substance 1 ppm | 50 (Mean titre of 2 strains) |
| HIV (2 strains) + β-SITOSTERYL-PALMITATE Concentrate 50 ppm | 76 (Mean titre of 2 strains) |

-continued

| TEST SUBSTRATE | | RESIDUAL HIV TITRE ($CCID_{50}$) (Mean titre from 3 cultures) |
|---|---|---|
| Active substance | 0.5 ppm | |
| HIV (2 strains) + | | 120 |
| β-SITOSTERYL-PALMITATE | | (Mean titre of 2 |
| Concentrate | 10 ppm | strains) |
| Active substance | 0.1 ppm | |

Residual HIV titres after preincubation during 3 h at +4° C.

For the applied test method cf. i.a.: Rudi Pauwels, Erik De Clercq et al.: "Sensitive and rapid assay on MT-4 cells for detection of antiviral compounds against the AIDS virus". Rega Institute for Medical Research, Katholieke Universiteit Leuven, 3000 Leuven, Belgium, Elsevier Science Publishers B.V. (Biomedical Division), 1987 (0166–0934/87/503.50); J.Virol. Methods 1987; 16, 171–85.

Also see: A. Bergamini, C. F. Perna, et al.: A tetrazolium-based colorimetric assay for quantification of HIV-induced cytopathogenicity in monocytemacrophages exposed to macrophage colony-stimulating factor. J.Virol. Methods, 1992; 40(3), 275–86.

Jay A. Levy: "HIV research: a need to focus on the right target", The Lancet, Vol. 345, Jun. 24, 1995, pp. 1619–21.

Molecular Cell Biology, second Edition, by J. Darnell, H. Lodish, D. Baltimore; Scientific American Books, Chapter 5: Viruses, Structure and Functions, pp. 177–188. New York, 1990 (W.H. Freeman & Co.).

8.0 Other Viruses 8.1 Human Cytomegalo-Virus (CMV)

The assay was conducted with human, embryonic Lung Fibroblasts as host cells, which were then infected with the human CMV-strain AD169.

The virus strain was incubated during 4 h at +4° C. with varying concentrations of the test substance $C_{16:0}$-β-Sitosteryl ester, formulated as a 1%-concentrate and diluted to aqueous microemulsions $10^{-3}$, $10^{-4}$ and $10^{-5}$. It was subsequently inoculated on monolayers of human embryonic lung fibroblasts (which are very susceptible to the CMV-virus). These host cells were grown in shell vials in minimal essential medium (MEM, GIBCO, Life Technologies), containing 10% fetal calf serum. A confluent culture was raised with 120,000 cells per shell-vial. The infection was effected by means of centrifugation during 45 minutes at 1'500 rpm at RT. Thereafter, the injection-suspension was eliminated and 1 ml medium MEM+2% FCS was added (same medium as before). The infected cell culture was maintained during 20 h at 37° C., in a 5%-$CO_2$-atmosphere.

At the end of incubation, the medium was eliminated, the pellets were harvested, fixed with 2% acetone/methanol and washed 3 times with PBS.

Quantification of the virucidal effect was measured with an immunofluorescence assay. To the vials was added the monoclonal antibody "Anti-P-72 CMV" (an immediate precursor protein [IEA, clone E 13, Argene Biosoft, BIOLINE, Torino] to the CMV, which can be traced in the infected cells already after 6 h of incubation). Incubation during 30 minutes at 37° C., in humid atmosphere.

This is followed by 3 washing operations with PBS and a second incubation with the fluorescence-marked antibody IgG goat anti-IgG mouse. This second incubation is conducted during 30 minutes at 37° C., as indicated above, and followed again by 3 washing operations with PBS. The probes are then mounted on glass with 50% glycerol in PBS.

At the same time, controls were prepared, with infected cells, under the same conditions, however without pretreatment with the test substance.

The number of IEA-positive cells was recorded. The nuclei which were positive against the CMV-specific antigen were counted by means of the fluorescence microscope, magnification 25×, in aqueous phase.

The assay resulted in a clear, dose-dependent, directly virucidal efficacy of the test substance. At the end of the test, the virus is no longer virulent enough for infecting the host-cells, which are very sensitive to the virus.

Results

VIRUCIDAL EFFICACY of the β-SITOSTERYL-PALMITATE (formulated as 1%-MARIGENOL ®-CONCENTRATE)

| CONTROLS: Number of the Antigens (anti P-72) | CONCENTRATION MICRO-EMULSION 1:1'000 = 1'000 ppm Conc. | CONCENTRATION MICRO-EMULSION 1:10'000 = 100 ppm of Conc. | CONCENTRATION MICRO-EMULSION 1:100'000 = 10 ppm of Conc. |
|---|---|---|---|
| 15'000 | 0 | 2 | 82'000 |

Number of the "positive nuclei" for the P-2

Assays conducted by Dottoressa Rossana CAVALLO, Istituto di Microbiologia, Università di Torino, July–November 1995.

8.2 Herpes-Virus (Herpes Simplex, HSV)

Assay Procedure

The antiviral/virucidal efficacy against HSV of an aqueous microemulsion prepared with appropriate MARIGENOL®-concentrates was assessed on a confluent monolayer culture of VERO cells (i.e. "African green monkey kidney cells"). The host cells were pretreated during 3 h at 4° C. with an inventive microemulsion or with culture medium alone and then infected with HSV at a constant dose of $10^4$ plaque forming units (PFU). After virus absorption during 1 h, and subsequent addition of 2% methylcellulose in order to limit virus spreading, cells were cultured in MEM medium+2% foetal calf serum for 48 h, then fixed and stained with 1% crystal violet in methanol. The reduction of viral titre was expressed as percent reduction of plaques of lysis observed in pre-treated cells, compared to controls.

Infection was also detected by IFA at 24 h after inoculation, using a Mab specific for a glycoprotein common to HSV-1/HSV-2 (clone FQ 12, Argene Biosoft, BIOLINE, Torino).

The following test substances were assessed as concentrates in aqueous dilution (starting with a microemulsion 1:100):

1% of $C_{20:0}$-β-SITOSTERYL ESTER

1% of QUERCETIN-PENTA-10-UNDECENOATE

1% of $C_{16:0}$-SITOSTERYL ESTER

1% of $C_{12:0}$-ERGOSTERYL ESTER

Results

| DILUTION | $C_{20:0}$-β-SITO ESTER (β-SITO ARACHIDATE) | QUERCETIN-PENTA-UN-DECENOATE | $C_{16:0}$-β-SITO ESTER (β-SITOST. PALMITATE) | $C_{12:0}$-ERGO ESTER (ERGOST. LAURATE) |
|---|---|---|---|---|
| 1:1'000 | Cell-Lysis | Cell-Lysis | Cell-Lysis | Cell-Lysis |
| 1:10'000 | 76% | 48% | 24% | 62% |
| 1:100'000 | 5% | 0% | 0% | 0% |

Percent reduction of plaques in VERO cell monolayers pre-treated with microemulsions compared to simple medium The results put in evidence a distinct direct action on the HS-virus-infected VERO host cells. The β-Sitosteryl arachidate concentrate, applied in aqueous dilution of $10^{-4}$, reduced the number of plaques by 76%, in comparison with the controls.

At this concentration of the test substance, no cell lysis due to the tested substances was taking place, neither in VERO cell layers, nor in the eternalised lymphocyte cultures of the MT-4-type.

Assays conducted by Dottoressa Rossana CAVALLO, Istituto di Microbiologia, Università di Torino, July 1995.

I claim:

1. A spontaneously dispersible concentrate, which if diluted with distilled water, 5% -glucose solution or physiological sodium salt solution, generates thermodynamically stable ultramicroemulsions, with nanosized micelles having a hydrodynamic radius of 2.2 to 3.0 nm, comprising the following components:

0.1 to 5% by weight of an ester of Baccatin-III, 10-Deacetylbaccatin-III or 14-OH-14-Deacetylbaccatin-III in accordance with one of the formulae (I) to (II):

wherein $R^1$ to $R^4$ can be replaced with hydrogen, acetyl or a $C_{6-32}$ alkylcarboxyl, a $C_{6-32}$ alkenylcarboxyl or a $C_{6-32}$ alkapolyenecarboxyl, 0 to 5% by weight of one or several pharmaceutically active principles, 0 to 25% by weight of a pharmaceutically acceptable solvent which acts as the hydrotropic agent or coemulgator, 50 to 90% by weight of a pharmaceutically acceptable surfactant or surfactant mixture, up to 10% of a vitamin or provitamin, up to 10% of a stabilizer, a radical scavenger and/or penetration enhancer.

2. A pharmaceutically useful preparation, comprising 90% by weight of the spontaneously dispersible concentrate as claimed in claim 1 and 10% by weight of pharmaceutically acceptable carriers, additives, excipients and/or diluents.

3. A spontaneously dispersible concentrate as claimed in claim 1, for use as a medicament having enhanced efficacy against tumors, eczemae and psoriasis and possessing improved therapeutic safety.

4. A spontaneously dispersible concentrate as claimed in claim 1, for use as a medicament having antiviral and/or virucidal efficacy and a potential for the increased absorption of exogenous activators, regulators or modulators.

5. A spontaneously dispersible concentrate as claimed in claim 1, comprising the following components:

0.5 to 5% by weight of one or several esters of Baccantin-III according to formula (I), 5 to 25% by weight of isopropylmyristate, isopropylpalmitate or neutral oil (oleum neutrale), or of one or several biotenside esters according to formula (VIII):

$$R^5\text{—COO—}R^6 \qquad (VIII)$$

in which $R^5$ is a $C_{2-18}$ alkyl, a $C_{3-18}$ alkenyl or a $C_{3-18}$ alkapolyene group and $R^6$ is Citronellyl, Farnesyl, Geranyl, Isophytyl or Phytyl, 0 to 45% by weight of a pharmaceutically acceptable phosphoric acid ester tenside, 5 to 90% by weight of the waterfree, tert.octylphenylpolyoxyethylene ether tenside having 9 to 10 oxyethylene groups and/or of polyoxyethylene-sorbitan-monolaurate.

6. A spontaneously dispersible concentrate as claimed in claim 1, comprising the following components:

0.5 to 5% by weight of one or several esters of Baccatin-III according to formula (I) in claim 1, 5 to 30% by weight of one or several biotenside esters according to formula (VIII):

$$R^5\text{—COO—}R^6 \qquad (VIII)$$

in which $R^5$ is a $C_{3-31}$ alkyl, a $C_{3-31}$ alkenyl or a $C_{3-31}$ alkapolyene group and $R^6$ is Citronellyl, Farnesyl, Geranyl, Isophytyl or Phytyl, 35 to 45% by weight of the waterfree, tert. octylphenylpolyoxyethylene ether tenside having 9 to 10 oxyethylene groups and/or of polyoxyethylene-sorbitan-monolaurate, 35 to 45% by weight of an alkylphenolpolyglykolether phosphate-tenside or of the tristyrylphenolpolyoxyethylene-18-phosphoric acid, TEA-salt-tenside.

7. A spontaneously dispersible concentrate according to claim 1, comprising:

1% by weight of an agent according to formulae (I) or (III),

7% by weight of ethyl alcohol, glycerol or 2-propanol and/or dimethylsulfoxide dried, 20% of Citronellyl-10-undecenoate or Citronellyl-laurate, 30% by weight by weight of the waterfree, tert.octylphenylpolyoxyethylene ether tenside having 9 to 10 oxyethylene groups, and/or of polyoxyethylenesorbitan-monolaurate, 42% by weight of the tristyrylphenolpolyoxyethylene-18-phosphoric acid, TEA-salt-tenside.

8. A pharmaceutical composition, which comprises 1 to 95% by weight of the spontaneously dispersible concentrate in accordance with claim 1, and which is present in one of the galenical forms, selected from the group of micropellets, granules, coated pills, suppositories ampuls or capsules.

9. A pharmaceutical composition according to claim 8, which comprises 44 parts of core material for granulation or pelleting, 25 parts of the concentrate and 31 parts of enteric, slow-release coating made from hydroxylpropyl-methylcellulose-acetate-succinate.

10. A pharmaceutical composition according to claim 8, which comprises 64 parts core material for granulation or pelleting and 36 parts of the concentrate and is filled into pharmaceutically appropriate capsules made from hyroxylpropyl-methylcellulose-acetate-succinate.

11. A pharmaceutical composition, which comprises 1 to 95% by weight of the spontaneously dispersible concentrate in accordance with claim 5, and which is present in one of the galenical forms, selected from the group of micropellets, granules, coated pills, suppositories, ampuls or capsules.

12. A pharmaceutical composition, which comprises 1 to 95% by weight of the spontaneously dispersible concentrate in accordance with claim 7, and which is present in one of the galenical forms, selected from the group of micropellets, granules, coated pills, suppositories, ampuls or capsules.

13. A pharmaceutical composition according to claim 1, which comprises 44 parts of core material for granulation or pelleting, 25 parts of the concentrate and 31 parts of enteric, slow-release coating made from hydroxylpropyl-methylcellulose-acetate-succinate.

14. A pharmaceutical composition according to claim 9, which comprises 64 parts core material for granulation or pelleting and 36 parts of the concentrate is filled into pharmaceutically appropriate capsules made from hydroxylpropyl-methylcellulose-acetate-succinate.

15. A pharmaceutical composition according to claim 1, which comprises 64 parts core material for granulation or pelleting and 36 parts of the concentrate is filled into pharmaceutically appropriate capsules made from hydroxylpropyl-methylcellulose-acetate-succinate.

* * * * *